(12) United States Patent
Schwartz

(10) Patent No.: US 8,597,352 B2
(45) Date of Patent: Dec. 3, 2013

(54) ARTICULAR CARTILAGE FIXATION DEVICE AND METHOD

(75) Inventor: Herbert E. Schwartz, Fort Wayne, IN (US)

(73) Assignee: Schwartz Biomedical, LLC, Fort Wayne, IN (US)

(*) Notice: Subject to any disclaimer, the term of this patent is extended or adjusted under 35 U.S.C. 154(b) by 69 days.

(21) Appl. No.: 10/598,223

(22) PCT Filed: Mar. 1, 2005

(86) PCT No.: PCT/US2005/006286
§ 371 (c)(1),
(2), (4) Date: Aug. 22, 2006

(87) PCT Pub. No.: WO2005/092208
PCT Pub. Date: Oct. 6, 2005

(65) Prior Publication Data
US 2008/0195205 A1 Aug. 14, 2008

Related U.S. Application Data

(60) Provisional application No. 60/549,748, filed on Mar. 3, 2004.

(51) Int. Cl.
*A61F 2/08* (2006.01)
(52) U.S. Cl.
USPC .................................. 623/14.12; 623/23.72
(58) Field of Classification Search
USPC ................ 623/13.11–13.19, 14.12; 606/232
See application file for complete search history.

(56) References Cited

U.S. PATENT DOCUMENTS

| 5,647,874 | A  | * | 7/1997 | Hayhurst ........................ 606/232 |
| 5,702,397 | A  |   | 12/1997 | Gable et al. |
| 6,179,840 | B1 |   | 1/2001 | Bowman |
| 6,972,027 | B2 | * | 12/2005 | Fallin et al. .................... 606/232 |
| 2004/0267314 | A1 | * | 12/2004 | Wolf et al. ..................... 606/230 |
| 2005/0113937 | A1 | * | 5/2005 | Binette et al. ............... 623/23.73 |
| 2005/0187577 | A1 | * | 8/2005 | Selvitelli et al. .............. 606/232 |

FOREIGN PATENT DOCUMENTS

| EP | 1129675 A2 | 9/2001 |
| WO | 03007788 A2 | 1/2003 |
| WO | 03007839 A2 | 1/2003 |

OTHER PUBLICATIONS

Supplemental Partial European Search Report for corresponding European application No. 05723940.0, mailed on May 6, 2011.

* cited by examiner

*Primary Examiner* — David Isabella
*Assistant Examiner* — Joshua Levine
(74) *Attorney, Agent, or Firm* — Heslin Rothenberg Farley & Mesiti P.C.

(57) ABSTRACT

An articular cartilage fixation device and method for repairing and regenerating diseased or injured soft tissue such as articular cartilage of the knee, hip, shoulder, and the like. A cartilage flap or cartilage repair device is retained within the chondral or osteochondral defect for a sufficient amount of time such that the cartilage repair device can perform its function and facilitate an appropriate healing response. A plurality of biocompatible anchors are attached to a plurality of flexible members and are shaped to seat into the tissue beneath or near the defect such that the cartilage flap is retained within the defect.

22 Claims, 11 Drawing Sheets

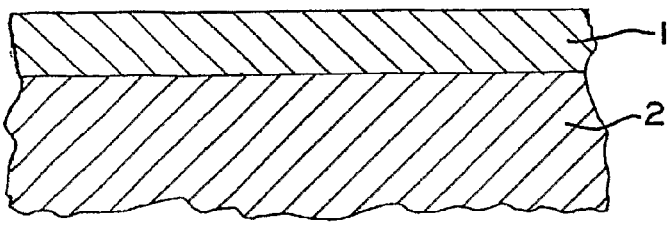
FIG_1
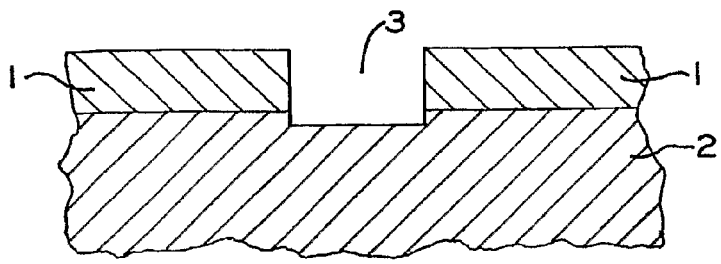
FIG_2
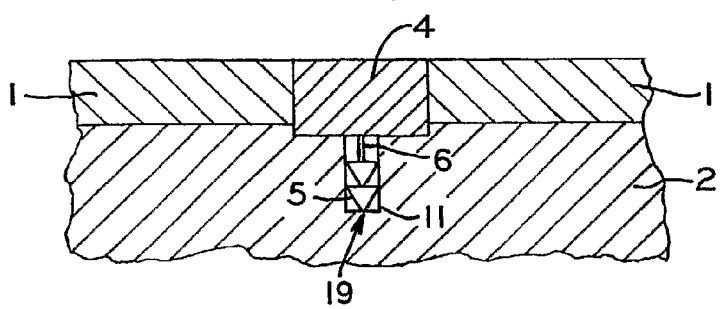
FIG_3
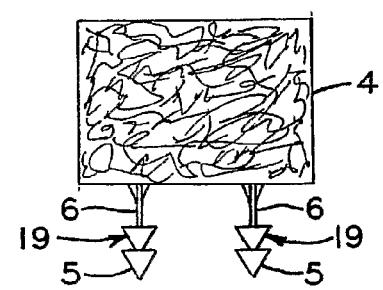
FIG_4
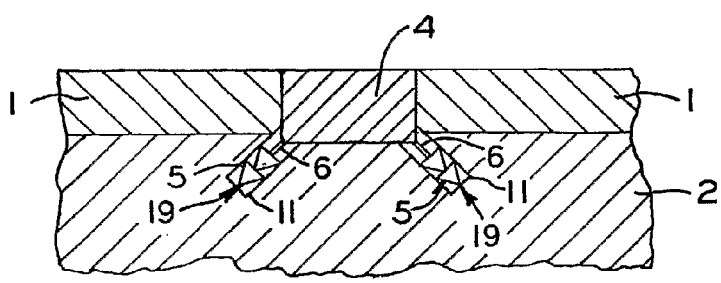
FIG_5
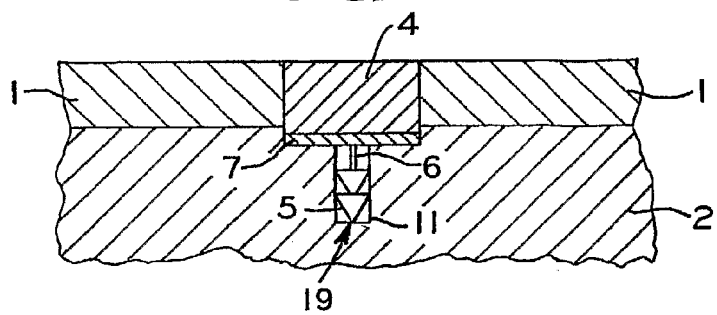
FIG_6

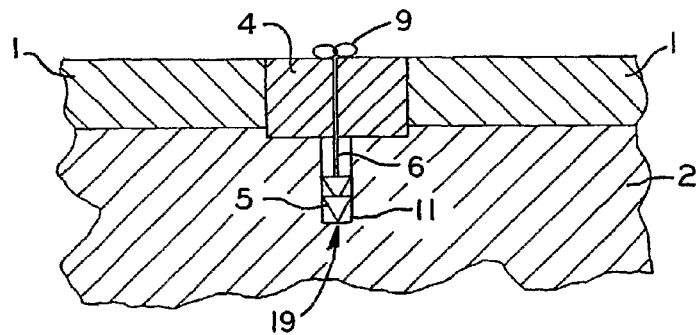
FIG_11
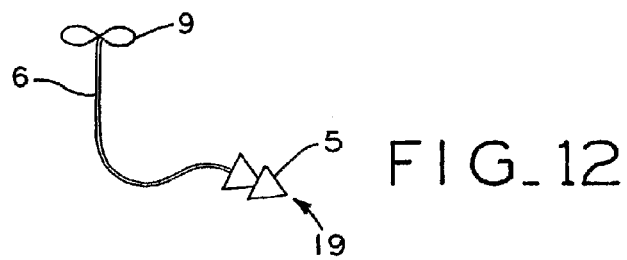
FIG_12
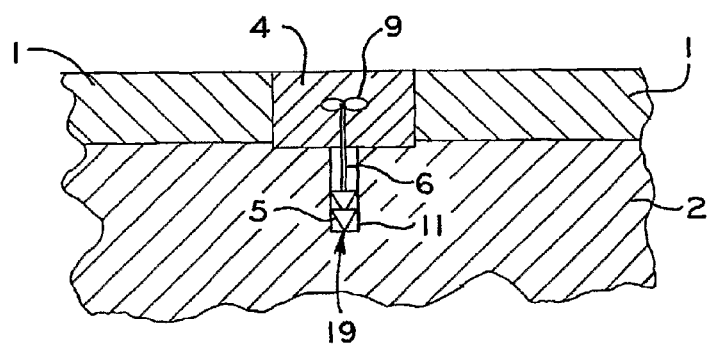
FIG_13
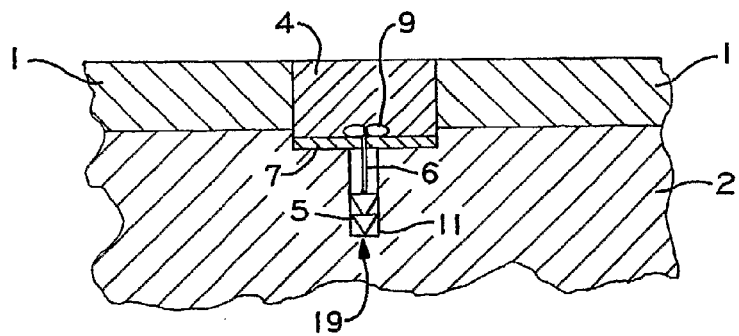
FIG_14

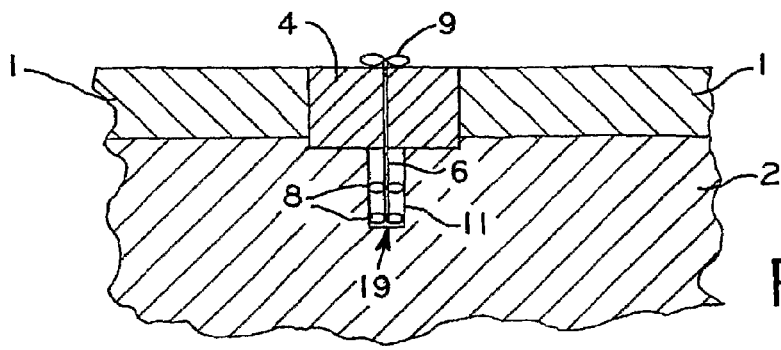
FIG_15
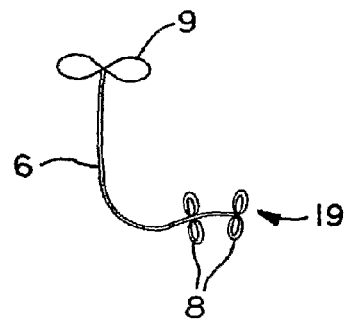
FIG_16
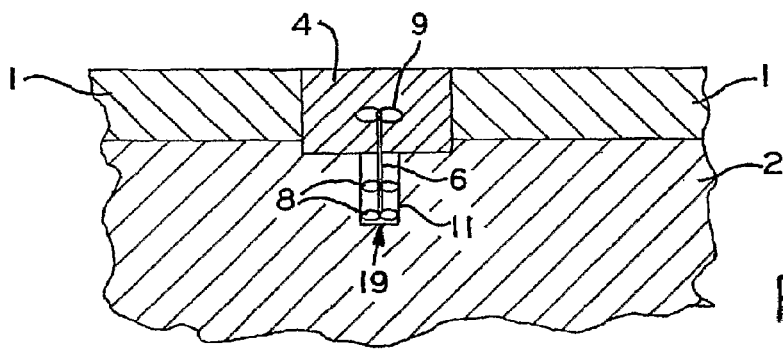
FIG_17
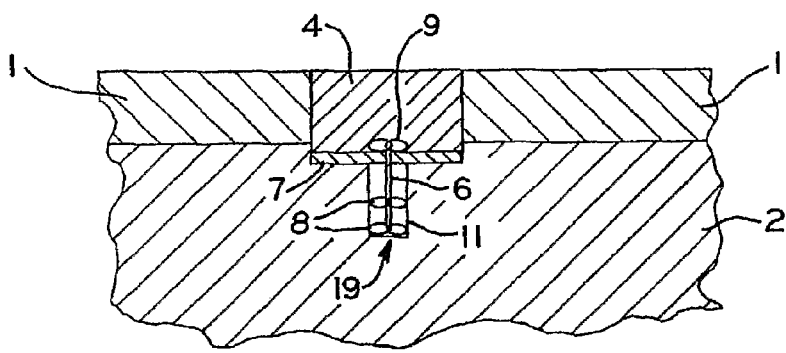
FIG_18

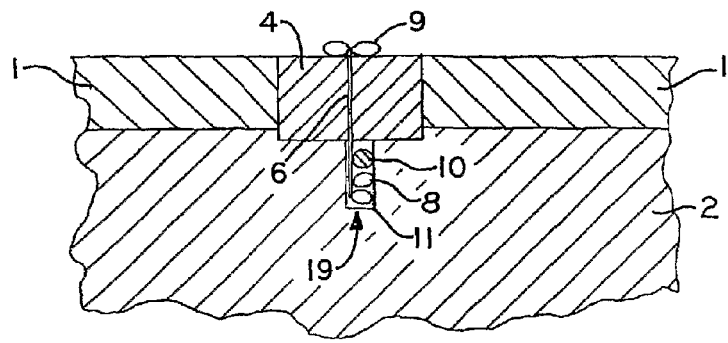
FIG_19
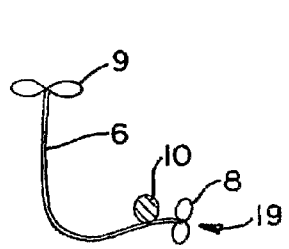
FIG_20
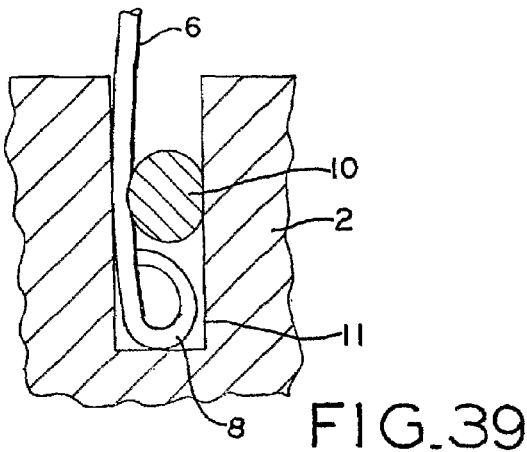
FIG_39
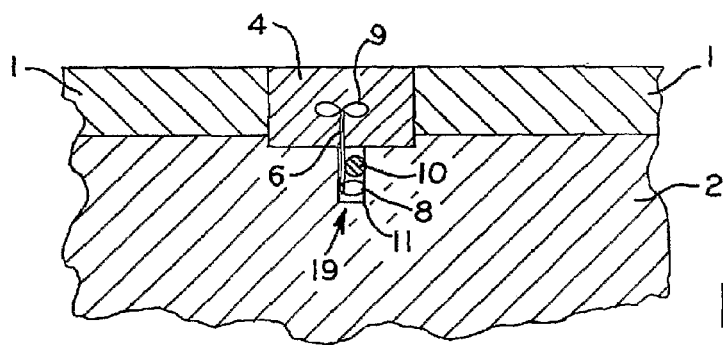
FIG_21
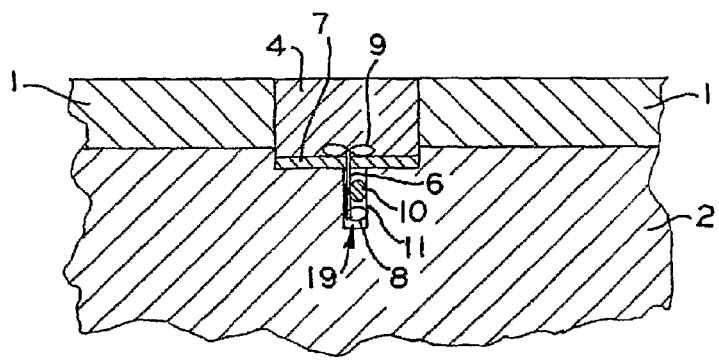
FIG_22

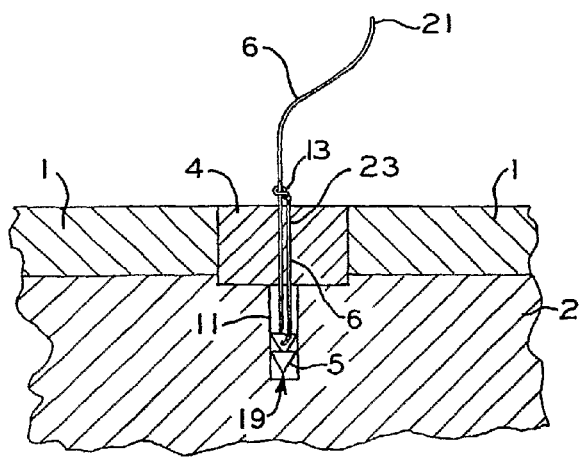
FIG_27
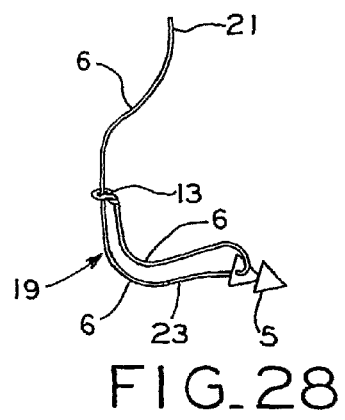
FIG_28
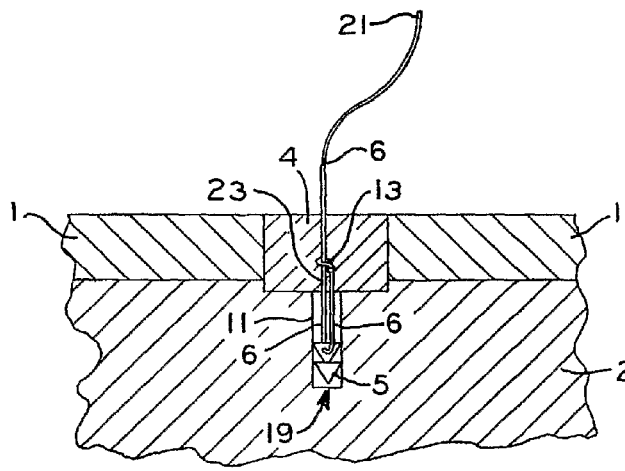
FIG_29
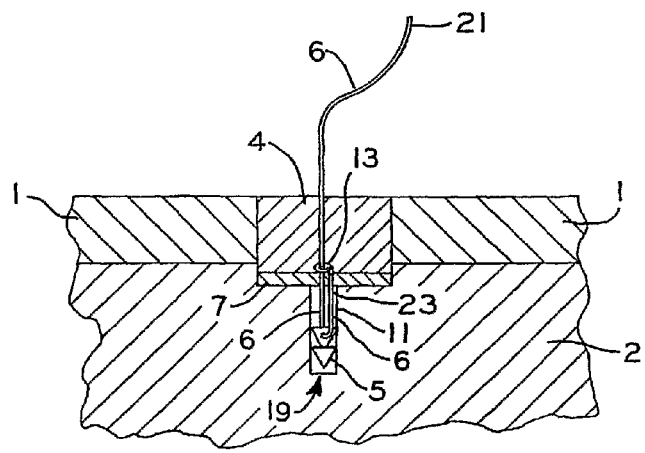
FIG_30

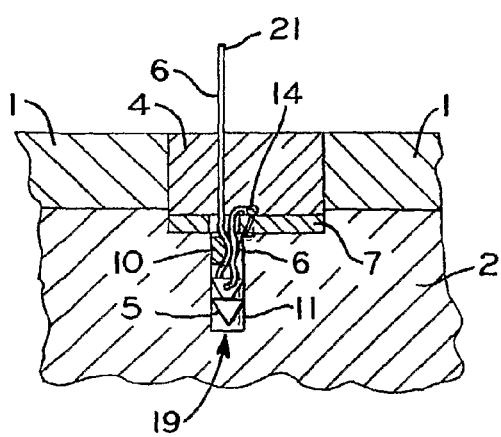
FIG_35
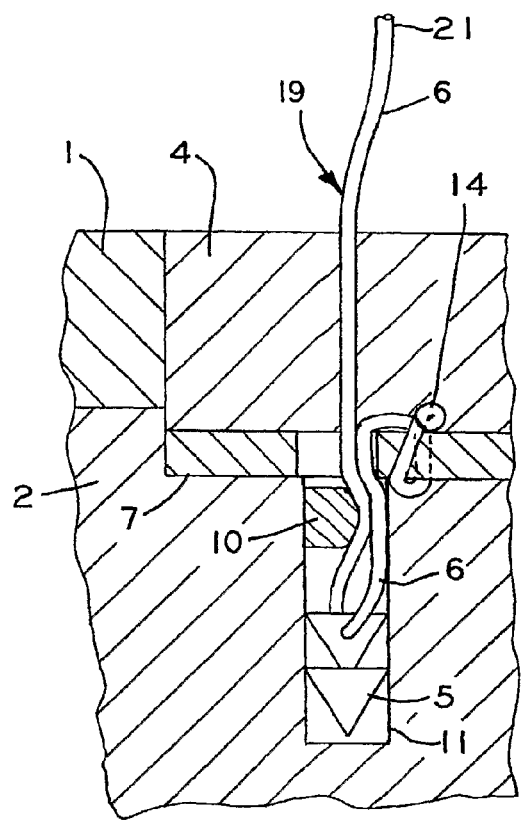
FIG_36
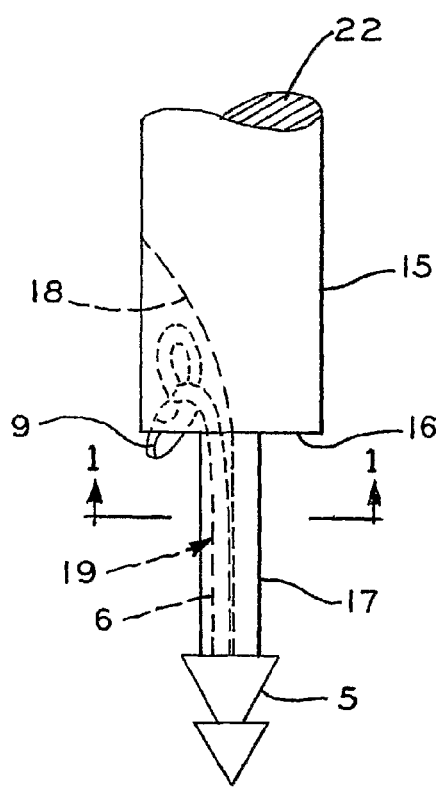
FIG_37
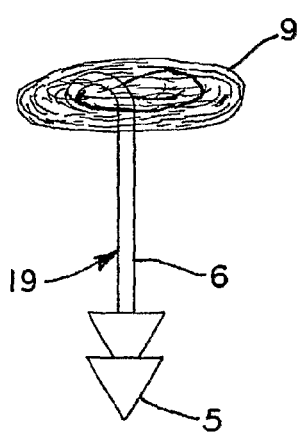
FIG_38

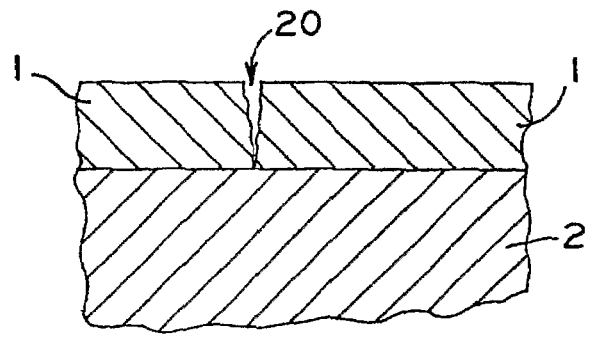
FIG_40
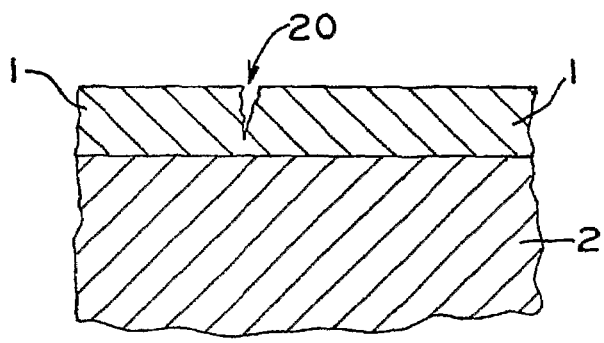
FIG_41
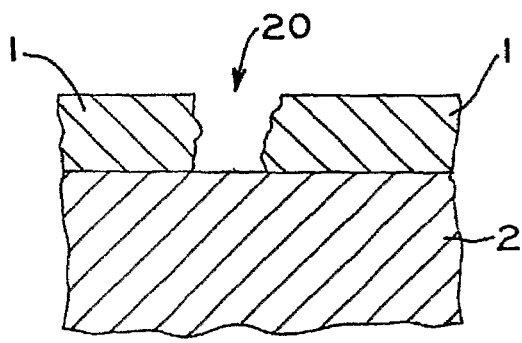
FIG_42
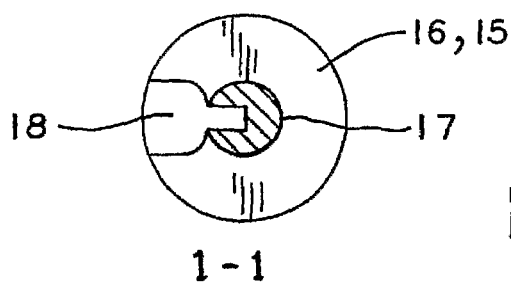
FIG_43

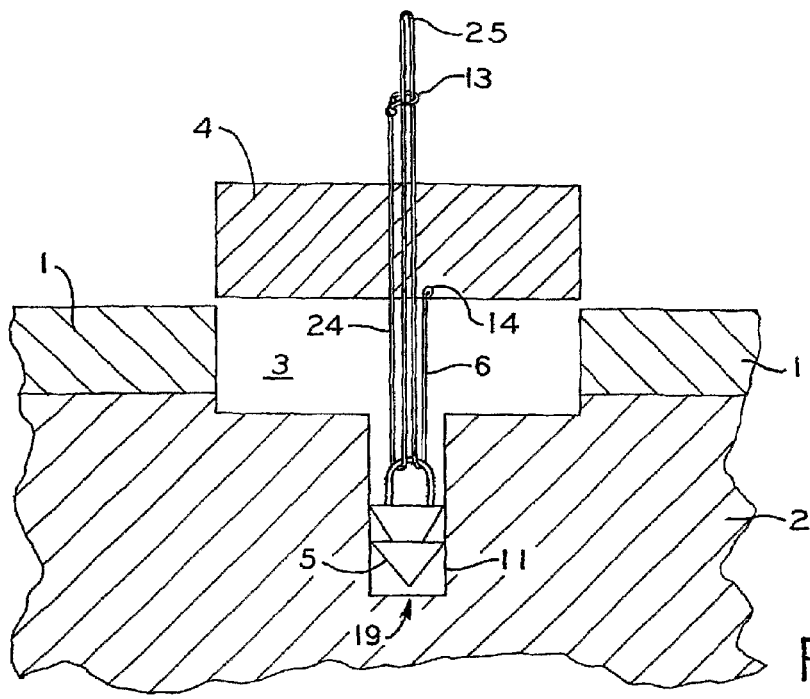
FIG_44
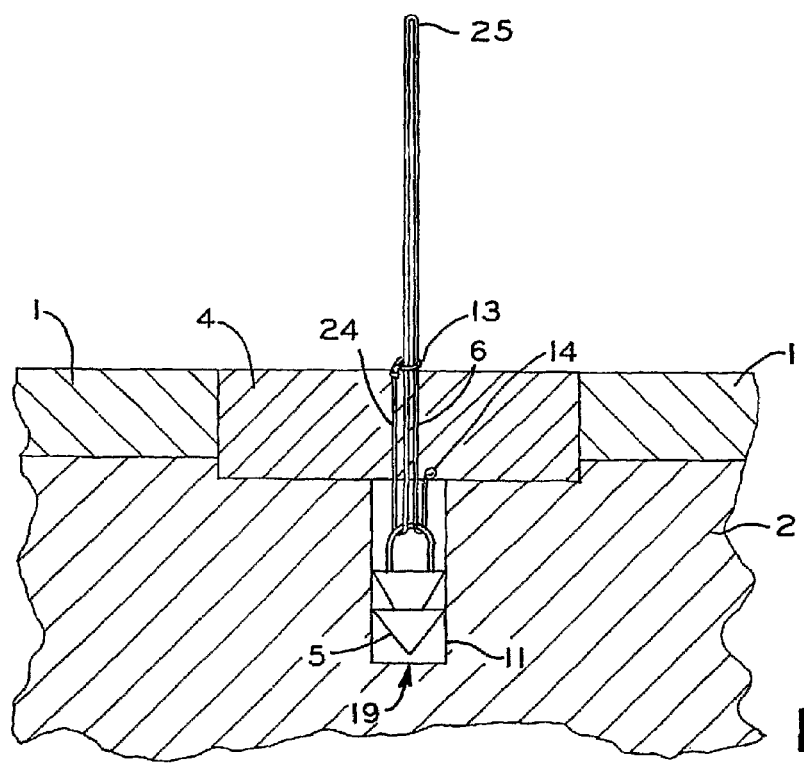
FIG_45

ARTICULAR CARTILAGE FIXATION DEVICE AND METHOD

CROSS-REFERENCE TO RELATED APPLICATIONS

This application is a §371 filing of PCT application PCT/US05/06286 filed on Mar. 1, 2005, which claims priority from U.S. Provisional Application 60/549,748, filed on Mar. 3, 2004. The disclosures of these applications are included by reference herein in their entirety.

FIELD OF INVENTION

The present invention relates generally to surgical devices for approximating, repairing, or regenerating damaged or diseased soft tissue (i.e. articular cartilage, fibrocartilage, collagenous structures, ligaments, tendons, etc. . . . ) of joints (knee, hip, shoulder, temporomandibular joint, spine, fingers, ankle, toes, etc. . . . ), and to surgical methods using such devices.

BACKGROUND OF INVENTION

Cartilage is a functional tissue found in diarthrodial joints at the ends of opposing bones and participates in load transmittal and load distribution between the bone ends. In addition to load distribution, cartilage also provides a nearly frictionless surface for the opposing bones to actuate upon so that ease of joint articulation is maximized. This type of articulating or articular cartilage is known as hyaline cartilage.

Hyaline cartilage is an aneural, avascular tissue with a very low propensity to heal after being injured or diseased. Therefore, small defects that occur in articular cartilage have a tendency to grow into larger defects. Being an aneural tissue, this progression of defects from small to large often occurs without the knowledge of the patient because of the lack of pain. When the defect reaches a size or level such that the patient begins to feel discomfort, defect progression often has occurred.

The standard of care to treat such defects includes surgical debridement of the defect area, often followed by microfracture or microdrill of the subchondral bone to induce bleeding from the bone. This treatment results in a fibrocartilage scar formation within the defect initially. However, the biomechanical properties of the repair scar tissue are inferior to that of the adjacent normal articular cartilage; therefore, the repair tissue eventually wears away to expose the defect. Since the repair tissue biomechanical properties are weaker than native articular cartilage, the articular cartilage surrounding the defect area tends to become overloaded because the repair tissue is not carrying as much load as normal articular cartilage would carry in the defect area. The result often is that as time progresses a larger defect forms than was originally present during the initial surgery.

Another treatment that is sometimes used by surgeons is known as mosaicplasty. This procedure involves removing cores of cartilage and bone from the defect site and press-fit into these holes with properly sized cartilage and bone plugs from non-weight bearing areas of the patient's knee. One or more such plugs can be used at a time. This procedure is very controversial because it is dependent on the skill of the surgeon and because the use of multiple plugs results in areas of the defect that are not covered. So, the patient's body will typically fill the gaps between and around the plugs with inferior scar tissue. There is also concern surrounding the integration of the plug with the recipient site as well as concern of the donor sites healing.

Another treatment option that is employed by surgeons uses allografts from donor human knees. Allografts must be size-matched properly to restore the patient's normal kinematics and anatomy. These grafts are also press-fit into holes that have been cored into the defect area of the recipient patient. As with mosaicplasty, similar concerns are present in addition to the concern of disease transmission from the donor human.

Another treatment option that is employed by surgeons is known as the Carticel™ procedure. This procedure is a two step process that involves harvesting cartilage from a non-weight bearing area of the knee, isolating chondrocytes (cartilage producing cells) from the tissue, and expanding (or culturing) these cells to acquire a large concentration of cells. After about 3 or 4 weeks, the patient returns to the hospital for the second step of the procedure which is the implantation stage. During this portion of the procedure, the defect area is carefully debrided, taking care to remove all of the cartilage from the defect and to not perforate or compromise the subchondral bone. Periosteum is harvested from the patient's tibia typically and sutured over the defect, leaving a small portion unsutured so that the expanded cells can be injected into the covered defect site. After the cells ale carefully injected into the defect site, the periosteum is completely sutured and the edges of the periosteal flap are sealed with fibrin glue.

Another type of cartilage that is found within joints is known as fibrocartilage. Fibrocartilage can be present intraarticularly in the form of a disc (spine, ternporo-mandibular joint), meniscus (knee), labrum (shoulder, hip), etc. . . . In the knee, the meniscus is a semi-lunar, wedge shaped tissue that sits on top of the tibia and articulates with the tibia and femur during gait activities. It acts as a shock absorber between the femur and tibia and distributes the compressive and shear loads from the curved condyles of the femur to the relatively flat plateau of the tibia. Similar to articular cartilage, much of the meniscus is avascular and aneural. However, the meniscus has three zones: red zone, red/white zone, and white zone. The red zone refers to approximately the outer peripheral third of the meniscus. This zone is rich in blood supply. The white zone can be found in the approximate inner peripheral third of the meniscus and is void of blood supply, and the red/white zone can be found in the approximate middle third and has some blood supply.

Injuries and pathology occur in the meniscus that manifest themselves in the forms of tears and degeneration. Various types and degrees of tears can and do occur often as a result of some twisting action in the knee or as a result of repetitive impact over time. Meniscus degeneration can also occur as a result of aging so that soft places develop in the tissue such that even common activities such as squatting can cause meniscal tears.

Common surgical procedures for treating meniscal damage include repairing the tears and complete or partial meniscectomies. Repairing the tear is commonly performed when the tear is a longitudinal vertical tear in the vascular (or red) zone of the meniscus. The tear is stabilized with suture or some other repair device such that the relative motion of the tear faces is minimized or eliminated during load bearing. Many devices and surgical procedures exist for repairing meniscal tears by approximating the faces of the meniscal tear. Examples of such devices and procedures are disclosed in the following U.S. Pat. Nos. 6,319,271; 6,306,159; 6,306, 156; 6,293,961; 6,156,044; 6,152,935; 6,056,778; 5,993,475; 5,980,524; 5,702,462; 5,569,252; 5,374,268; 5,320,633; and 4,873,976. Meniscectomies involve the surgical removal of part or all of the meniscus. Such procedures have commonly been performed in the case of "unrepairable" or complex tears such as radial tears, horizontal tears, vertical longitudinal tears outside the vascular zone, complex tears, defibrillation, and/or degeneration. Meniscectomies typically provide immediate pain relief and restoration of knee function to the patient; however, with the absence of the meniscus, the long term effect on the knee can be cartilage wear on the condylar or tibial plateau surfaces and the eventual development of an arthritic condition such as osteoarthritis.

Other types of soft tissue that are commonly repaired by surgeons are ligaments and tendons. These soft tissues are typically attached to bone and must sometimes be reattached to bone if they are injured or become degenerative. Also, these tissues must sometimes be reattached to soft tissue if the injury or degeneration is mid-substance (i.e. occurs within the soft tissue . . . not at the bone attachment site). Common surgical procedures to repair these types of injuries include attaching soft tissue to bone with suture that is held in holes that are created through the bone (i.e. bone tunnels) or with suture that is attached to suture anchors. Common surgical procedures that are used to attach soft tissue to soft tissue include suturing, stapling, adhesives, suturing through scaffolds or reinforcement meshes.

SUMMARY OF THE INVENTION

The present invention is a device that can be used in the repair and regeneration of diseased or injured soft tissue such as articular cartilage of the knee, hip, shoulder, temporomandibular joint (TMJ), spine, fingers, wrist, ankle, etc. . . .

It is an objective of the present invention to fixate a cartilage repair device (ox implant) or a cartilage flap to the subchondral bone to facilitate repair or regeneration of the chondral or osteochondral defect. The cartilage repair device (or implant) or cartilage flap is approximated and retained within the chondral or osteochondral defect for an adequate amount of time such that the cartilage repair device (or implant) can perform its function and facilitate the appropriate healing response.

It is also an objective of the present invention to be comprised of a biocompatible anchor and a biocompatible flexible member that extends proximally from the biocompatible anchor to within or through the cartilage repair device or implant. Prior to surgery, the proximal portion of the flexible member is attached or is integrated within the cartilage repair device or implant. For instance, if the cartilage repair device (or implant) were composed completely or partially of a nonwoven material, the flexible member could be an extension of the nonwoven material. The distal end of the flexible member is attached to the biocompatible anchor. The anchor could be cannulated or non-cannulated. One or more of such flexible members and anchors could extend from the cartilage repair device or implant. The biocompatible anchor is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention for the cartilage repair device (or implant) to have a rigid or semi-rigid base that is attached to the cartilage repair device (or implant) and to which the proximal end of the flexible member is attached, and the distal end of the flexible member is attached to the biocompatible anchor. The anchor could be cannulated or non-cannulated. One or more of such flexible members and anchors could extend from the rigid or semi-rigid base of the cartilage repair device or implant. The biocompatible anchor is positioned and fixed into the subchondral bone immediately below—or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible anchor and a biocompatible flexible member that extends proximally from the biocompatible anchor to within or through the cartilage repair device or implant. Prior to surgery, the proximal portion of the flexible member is attached to or is integrated within the cartilage repair device or implant. For instance, if the cartilage repair device (or implant) were composed completely or partially of a nonwoven material, the flexible member could be an extension of the nonwoven material. The distal end of the flexible member is attached to the biocompatible anchor. The anchor is comprised of a knot or knots tied or attached to the distal end of the flexible member or the anchor could be woven or nonwoven pieces of biocompatible material that may or may not be attached to the flexible member. One or more of such flexible members and anchor knots could extend from the cartilage repair device or implant. The biocompatible anchor knot is positioned and fixed into the subchondral bone immediately below or adjacent to the chondral or osteochondral defect or is fixed into tie adjacent cartilage such that the cartilage repair device (or implant) is fixed into the chondral or osteochondral defect.

It is also an objective of the present invention for the cartilage repair device (or implant) to have a rigid or semi-rigid base that is attached to the cartilage repair device (or implant) and to which the proximal end of the flexible member is attached, and the distal end of the flexible member is comprised of one or more anchoring knots. One or more of such flexible members and anchor knots could extend from the rigid or semi-rigid base of the cartilage repair device or implant. The anchor knot(s) is(are) designed to wedge and to be positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible flexible member proximal end that is composed of a knot either tied to the cartilage repair device (or implant) or a knot that is sized such that it will not pass completely through the cartilage repair device or implant. The knot could also contain a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. The biocompatible anchor is positioned and fixed into the subchondral bone immediately below or adjacent to the chondral or osteochondral defect or is fixed into the adjacent cartilage such the cartilage repair device (or implant) is fixed into the chondral or osteochondral defect.

It is also an objective of the present invention for the cartilage repair device (or implant) to have a rigid or semi-rigid base that is attached to the cartilage repair device (or implant) and to which the proximal end of the flexible member is attached, and the distal end of the flexible member is attached to the biocompatible anchor. The anchor could be cannulated or non-cannulated. One or more of such flexible members and anchors could extend from the rigid or semi-rigid base of the cartilage repair device or implant. The biocompatible anchor is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible flexible member proximal end that is composed of a knot either tied to the cartilage repair device (or implant) or a knot that is sized such that it will not pass completely through the cartilage repair device or implant. The knot could also contain a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. The anchor is comprised of one or more knots on the distal end of the flexible member and is positioned and fixed into the subchondral bone immediately below or adjacent to the chondral or osteochondral defect or is fixed into the adjacent cartilage such the cartilage repair device (or implant) is fixed into the chondral or osteochondral defect. The anchor could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above.

It is also an objective of the present invention for the cartilage repair device (or implant) to have a rigid or semi-rigid base that is attached to the cartilage repair device (or implant) and through which the proximal end of the flexible member protrudes but is prevented from advancing through due to a knot in the proximal end of the flexible member or a space filling entity (i.e. bead, wedge, rectangular or square component, etc. . . . ) attached to the proximal end of the flexible member. The space filling entity could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. The distal end of the flexible member is comprised of one or more anchoring knots. One or more of such flexible members and anchor knots could extend from the rigid or semi-rigid base of the cartilage repair device or implant. The anchor knot(s) is(are) designed to wedge and be positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible wedging component and a biocompatible flexible member that extends proximally to within or through the cartilage repair device or implant. Prior to surgery, the proximal portion of the flexible member is attached or is integrated within the cartilage repair device or implant. For instance, if the cartilage repair device (or implant) were composed completely or partially of a nonwoven material, the flexible member could be an extension of the nonwoven material. The distal end of the flexible member can be comprised of a knot or other space filling entity such that it can be wedged against the wall of a hole created in the bone or tissue when a wedging component is placed into the hole created previously or by the insertion of the distal end of the flexible member. The wedging component could be cannulated or non-cannulated and could be round, oval, rectangular, square, triangular, trapezoidal, pyramidal, etc. . . . The wedging component could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. One or more of such flexible members could extend from the cartilage repair device (or implant) and be placed in the same or different anchoring holes with one or more wedging components. The distal end of the flexible member is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention for the cartilage repair device (or implant) to have a rigid or semi-rigid base that is attached to the cartilage repair device (or implant) and to which the proximal end of the flexible member is attached, and the distal end of the flexible member can be comprised of a knot or other space filling entity such that it can be wedged against the wall of a hole created in the bone or tissue when a wedging component is placed into the hole created previously or by the insertion of the distal end of the flexible member. The wedging component could be cannulated or non-cannulated and could be round, oval, rectangular, square, triangular, trapezoidal, pyramidal, etc. . . . The wedging component could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. One or more of such flexible members could extend from the cartilage repair device (or implant) and be placed in the same or different anchoring holes with one or more wedging components. The distal end of the flexible member is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible wedging component and a biocompatible flexible member that extends proximally to within or through the cartilage repair device or implant. The proximal portion of the flexible member is composed of a knot either attached to the cartilage repair device (or implant) or a knot that is sized such that it will not pass completely through the cartilage repair device or implant. The knot could also contain a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. The distal end of the flexible member can be comprised of a knot or other space filling entity such that it can be wedged against the wall of a hole created in the bone or tissue when a wedging component is placed into the hole created previously or by the insertion of the distal end of the flexible member. The wedging component could be cannulated or non-cannulated and could be round, oval, rectangular, square, triangular, trapezoidal, pyramidal, etc. . . .

The wedging component could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. One or more of such flexible members could extend from the cartilage repair device (or implant) and be placed in the same or different anchoring holes with one or more wedging components. The distal end of the flexible member is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention for the cartilage repair device (or implant) to have a rigid or semi-rigid base that is attached to the cartilage repair device (or implant) and through which the proximal end of the flexible member protrudes but is prevented from advancing through due to a knot in the proximal end of the flexible member or a space filling entity (i.e. bead, wedge, rectangular or square component, nonwoven ball, woven or knitted disc or cylinder, other nonwoven or woven or knitted structure, etc. . . . ) attached to the proximal end of the flexible member. The distal end of the flexible member is comprised of a knot or other space filling entity such that it can be wedged against the wall of a hole created in the bone or tissue when a wedging component is placed into the hole created previously or by the insertion of the distal end of the flexible member. The wedging component could be cannulated or non-cannulated and could be round, oval, rectangular, square, triangular, trapezoidal, pyramidal, etc. . . . The wedging component could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above. One or more of such flexible members could extend from the cartilage repair device (or implant) and be placed in the same or different anchoring holes with one or more wedging components. The distal end of the flexible member is positioned and fixed into the subchondral bone immediately below or adjacent to the chondral or osteochondral defect or is fixed into the adjacent cartilage such that the cartilage repair device (or implant) is fixed into the chondral or osteochondral defect.

It is also an objective of the present invention to be comprised of a biocompatible flexible member that is looped through a biocompatible anchor and tied back on itself proximally with a slip knot or knots. The proximal ends of the flexible member pass completely or partially through the cartilage repair device or implant. The distal end of the looped flexible member passes through the anchor, and the anchor is positioned and fixed into the subchondral bone immediately below or adjacent to the chondral or osteochondral defect or is fixed into the adjacent cartilage. As the free proximal end of the flexible member is pulled, the slip knot advances distally down the flexible member as the biocompatible anchor allows the flexible member to slide through it (acting as a pulley) to fix the cartilage repair device (or implant) is into the chondral or osteochondral defect. One or more of such flexible members and anchors could protrude from the cartilage repair device (or implant) to facilitate the fixation of the device or implant.

It is also an objective of the present invention for the cartilage repair device (or implant) to have a rigid or semi-rigid base that is attached to the cartilage repair device (or implant) and through which the flexible member is looped such that both proximal ends of the flexible member are passed. The distal end of the flexible member is passed through a biocompatible anchor such that the anchor acts as a pulley. The anchor could be cannulated or non-cannulated. Prior to implantation, one of the proximal ends of flexible member is attached to the other proximal end via a slip knot. The proximal ends of the flexible member pass completely or partially through the cartilage repair device or implant. The biocompatible anchor is positioned into the subchondral bone immediately below or adjacent to the chondral or osteochondral defect or is fixed into the adjacent cartilage. As the free proximal end of the flexible member is pulled, the slip knot advances distally as the biocompatible anchor allows the flexible member to slide through it (acting as a pulley) to fix the cartilage repair device (or implant) is into the chondral or osteochondral defect. One or more of such flexible members and anchors could protrude from the cartilage repair device (or implant) to facilitate the fixation of the device or implant.

It is also an objective of the present invention to be comprised of a biocompatible flexible member that is looped through a biocompatible anchor. One of the proximal ends of the flexible member pass completely through the cartilage repair device or implant; whereas, the other proximal end of the flexible member is attached to the cartilage repair device or implant. The distal end of the looped flexible member passes through the anchor, and the anchor is positioned and fixed into the subchondral bone immediately below or adjacent to the chondral or osteochondral defect or is fixed into the adjacent cartilage. As the free proximal end of the flexible member is pulled, the proximal end of the flexible member that is attached to the cartilage repair device (or implant) advances distally along with the cartilage repair device (or implant) toward the biocompatible anchor as the biocompatible anchor allows the flexible member to slide through it (acting as a pulley) so that the cartilage repair device (or implant) is approximated into the chondral or osteochondral defect. When the cartilage repair device (or implant) is in the desired position, a wedging device is slid down or along the flexible member and pushed into the hole used for the biocompatible anchor such that the proximal end of the flexible member that is attached to the cartilage repair device (or implant) is locked in place. One or more of such flexible members and anchors could protrude from the cartilage repair device (or implant) to facilitate the fixation of the device or implant.

It is also an objective of the present invention for the cartilage repair device (or implant) to have a rigid or semi-rigid base that is attached to the cartilage repair device (or implant) and through which the flexible member is looped such that one proximal end of the flexible member is passed and the other proximal end of the flexible member is attached to the rigid or semi-rigid base. The distal end of the flexible member is passed through a biocompatible anchor such that the anchor acts as a pulley. The anchor could be cannulated or non-cannulated. The free proximal end of the flexible member passes completely through the cartilage repair device or implant. The biocompatible anchor is positioned into the subchondral bone immediately below or adjacent to the chondral or osteochondral defect or is fixed into the adjacent cartilage. As the free proximal end of the flexible member is pulled, the proximal end of the flexible member along with the rigid or semi-rigid base and cartilage repair device (or implant) advance distally as the biocompatible anchor allows the flexible member to slide through it (acting as a pulley) to approximate the cartilage repair device (or implant) into the chondral or osteochondral defect. When the cartilage repair device (or implant) is in the desired position, a wedging device is slid down or along the flexible member and pushed into the hole within the rigid or semi-rigid base or into the hole used for the biocompatible anchor such that the proximal end of the flexible member that is attached to the cartilage repair device (or implant) is locked in place. One or more of such flexible members and anchors could protrude from the cartilage repair device (or implant) to facilitate the fixation of the device or implant.

It is also an objective of the present invention to be comprised of a biocompatible anchor, a biocompatible flexible member that extends proximally from the biocompatible anchor to within or through the cartilage repair device or implant, and a biocompatible retaining component positioned on the proximal end of the flexible member. Prior to surgery, the retaining or stopping component is attached to the flexible member, and the distal end of the flexible member is attached to the biocompatible anchor. The anchor could be cannulated or non-cannulated. The retaining component could be composed of a nonwoven piece of biocompatible material that is attached to the flexible member or a woven piece of biocompatible material that is attached to the flexible member or a knitted piece of biocompatible material that is attached to the flexible member or any combination of the above. The purpose of the retaining or stopping component is to act as a shoulder device on the proximal end of the flexible member against which tension can be applied through the flexible member such that fixation can be accomplished with this device by maximizing the pull-through force of the retaining or stopping component.

It is also an objective of the present invention for the biocompatible anchor, the flexible member, the retaining or stopping component, and all other components of the invention to be manufactured or derived from the same materials or for some or each component to be made of different materials. The biocompatible anchor consists of at least one of the following: a tack with or without barbs, a dart with or without barbs, a flared device with or without barbs, a pronged device with or without barbs, a screw, a bead, a knot. The biocompatible flexible member includes at least one of the following: a suture of fixed length with a knot and/or a retaining component on the proximal end, a synthetic polymer or copolymer of fixed length with a knot and/or a retaining component on the proximal end, a naturally occurring collagen containing material of fixed length with a knot and/or retaining component on the proximal end, a processed collagen containing material of fixed length with a knot and/or retaining component on the proximal end. The biocompatible flexible material can be looped or un-looped. The biocompatible stopping device and retaining component consist of at least one of the following: a rod, a cylinder, an elliptical rod, a bead, a flat plate, a knot or knots, a hook, a plurality of hooks, nonwoven ball, a woven or knitted ball, a nonwoven sheet, a woven or knitted sheet. Biocompatible refers to materials that are nonabsorbable (i.e. polyesters, polyethylene, ultra-high molecular weight polyethylene, nylon, prolene, polypropylene, homopolymers, copolymers, etc. . . . ) or absorbable (i.e. poly-L-lactic acid, polyglycolic acid, polydioxinone, polycaprilactone, polyesters, homopolymers, copolymers, etc. . . . ). Biocompatible also refers to materials that are naturally occurring such as extracellular matrix (ECM) materials such as submucosa from the intestine, bladder, etc. . . . It also refers to biological materials that contain collagen as a component. These materials can be crosslinked (chemically, irradiation, light, UV, microwave, etc. . . . ) or non-crosslinked. Biocompatible also refers to materials that are a combination of any of the aforementioned materials.

It is also an objective of the present invention to provide a method for repairing torn articular cartilage (chondral) flaps or defects or torn articular cartilage/bone (osteochondral) flaps or defects. Articular cartilage has an articulating surface and a surface that is in integrated into bone. A flap or defect results when articular cartilage has an inner surface that is disconnected from bone or when the bone has an inner surface that is disconnected from bone. The method comprises having a fixation device consisting of a biocompatible anchor and flexible member. After the flap or defect in the articular cartilage and/or in the cartilage/bone is located, the fixation device is implanted to approximate the two inner surfaces of the cartilage or cartilage/bone at the tear, with the flexible member (i.e. suture) extending across the tear and the anchor being located away from the tear and the stopping device or retaining component is located on top of or within the flap.

It is also an objective of the present invention to provide a method for repairing damaged or diseased articular cartilage (chondral) or articular cartilage/bone (osteochondral). Articular cartilage has an articulating surface and a surface that is in integrated into bone. When the damaged or diseased area is located, a portion of the damaged or diseased cartilage or cartilage and bone is removed, creating a chondral (cartilage only) or an osteochondral (cartilage and bone) defect. A cartilage repair device (or implant) can be placed in the defect. The method comprises having a fixation device consisting of a biocompatible anchor and flexible member that is or is not integrated within the cartilage repair device or implant. The fixation device is implanted to approximate the inner surface of the cartilage repair device (or implant) to the surface of the chondral or osteochondral defect, with the flexible member extending across the cartilage repair device surface/chondral or osteochondral surface interface and the anchor being located away from this interface.

It is also an objective of the present invention to be applied toward the fixation of other soft and cartilagenous tissue implants (i.e. meniscus, temporomandibular joint disc, spinal disc, ligaments, tendons, etc. . . . ) to native tissue (bone or soft tissue).

BRIEF DESCRIPTION OF DRAWINGS

The invention will be better understood by reference to the figures wherein like numbers denote like parts throughout and wherein:

FIG. 1 is cross sectional schematic of normal articular cartilage and subchondral bone.

FIG. 2 is a cross sectional schematic of cartilage and subchondral bone with a defect shown through the cartilage and into a portion of the subchondral bone.

FIG. 3 is a cross sectional schematic of a cartilage repair device (or implant) or cartilage flap that is implanted into a cartilage and bone defect. It is fixed to the subchondral bone using one embodiment of the present invention directed perpendicularly to the articulating surface.

FIG. 4 is a cross sectional schematic of a cartilage repair device (or implant) or cartilage flap with one embodiment of the present invention shown as an integral part of or is attached to the cartilage repair device (or implant) or cartilage flap.

FIG. 5 is a cross sectional schematic of a cartilage repair device (or implant) or cartilage flap that is implanted into a cartilage and bone defect. It is fixed to the subchondral bone using one embodiment of the present invention directed at an angle that is not perpendicular to the articulating surface.

FIG. 6 is a cross sectional schematic of a cartilage repair device (or implant) or cartilage flap with a rigid or semi-rigid base that is attached to the implant. The assembly is implanted into a cartilage and bone defect. It is fixed to the subchondral bone using one embodiment of the present invention directed at an angle that is not perpendicular to the articulating surface.

FIG. 11 is a cross sectional schematic of a cartilage repair device (or implant) or cartilage flap that is implanted into a cartilage and bone defect. It is fixed to the subchondral bone using the third embodiment of the present invention.

FIG. 12 is a perspective view of the third embodiment of the present invention.

FIG. 13 is a cross sectional schematic of a cartilage repair device (or implant) or cartilage flap that is implanted into a cartilage and bone defect. It is fixed to the subchondral bone using the third embodiment of the present invention.

FIG. 14 is a cross sectional schematic of a cartilage repair device (or implant) or cartilage flap with a rigid or semi-rigid base that is attached to the implant. The assembly is implanted into a cartilage and bone defect. It is fixed to the subchondral bone using the third embodiment of the present invention.

FIG. 15 is a cross sectional schematic of a cartilage repair device (or implant) or cartilage flap that is implanted into a cartilage and bone defect. It is fixed to the subchondral bone using the fourth embodiment of the present invention.

FIG. 16 is a perspective view of the fourth embodiment of the present invention.

FIG. 17 is a cross sectional schematic of a cartilage repair device (or implant) or cartilage flap that is implanted into a cartilage and bone defect. It is fixed to the subchondral bone using the fourth embodiment of the present invention.

FIG. 18 is a cross sectional schematic of a cartilage repair device (or implant) or cartilage flap with a rigid or semi-rigid base that is attached to the implant. The assembly is implanted into a cartilage and bone defect. It is fixed to the subchondral bone using the fourth embodiment of the present invention.

FIG. 19 is a cross sectional schematic of a cartilage repair device (or implant) or cartilage flap that is implanted into a cartilage and bone defect. It is fixed to the subchondral bone using the fifth embodiment of the present invention.

FIG. 20 is a perspective view of the fifth embodiment of the present invention.

FIG. 21 is a cross sectional schematic of a cartilage repair device (or implant) or cartilage flap that is implanted into a cartilage and bone defect. It is fixed to the subchondral bone using the fifth embodiment of the present invention.

FIG. 22 is a cross sectional schematic of a cartilage repair device (or implant) or cartilage flap with a rigid or semi-rigid base that is attached to the implant. The assembly is implanted into a cartilage and bone defect. It is fixed to the subchondral bone using the fifth embodiment of the present invention.

FIG. 27 is a cross sectional schematic of a cartilage repair device (or implant) or cartilage flap that is implanted into a cartilage and bone defect. It is fixed to the subchondral bone using the seventh embodiment of the present invention.

FIG. 28 is a perspective view of the seventh embodiment of the present invention.

FIG. 29 is a cross sectional schematic of a cartilage repair device (or implant) or cartilage flap that is implanted into a cartilage and bone defect. It is fixed to the subchondral bone using the seventh embodiment of the present invention.

FIG. 30 is a cross sectional schematic of a cartilage repair device (or implant) or cartilage flap with a rigid or semi-rigid base that is attached to the implant. The assembly is implanted into a cartilage and bone defect. It is fixed to the subchondral bone using the seventh embodiment of the present invention.

FIG. 35 is a cross sectional schematic of a cartilage repair device (or implant) or cartilage flap with a rigid or semi-rigid base that is attached to the implant. The assembly is implanted into a cartilage and bone defect. It is fixed to the subchondral bone using the ninth embodiment of the present invention.

FIG. 36 is close-up view of FIG. 35.

FIG. 37 is a schematic of a delivery instrument tip for the delivery of the present invention into the tissue.

FIG. 38 is a schematic of another embodiment of the present invention.

FIG. 39 is a close-up cross section of FIG. 19.

FIG. 40 is a cross sectional schematic of a full thickness cartilage tear.

FIG. 41 is a cross sectional schematic of a partial thickness cartilage tear.

FIG. 42 is a cross sectional schematic of a full thickness cartilage defect.

FIG. 43 is section 1-1 of an insertion instrument as indicated in FIG. 37.

FIG. 44 is a cross sectional schematic of a cartilage repair device (or implant) or cartilage flap that is in process of being implanted into a cartilage and bone defect using an embodiment of the present invention that comprises a double looped suture or flexible member.

FIG. 45 is a cross sectional schematic of the same device of FIG. 44 with the cartilage repair device (or implant) or cartilage flap approximated to the surface of the defect.

DETAILED DESCRIPTION OF THE ILLUSTRATED EMBODIMENTS

Figure 7:
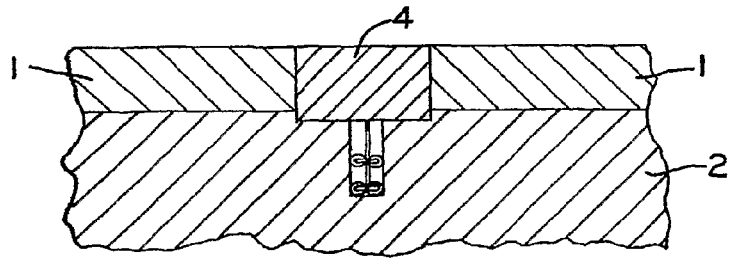
FIG. 7 is a cross sectional schematic of a cartilage repair device (or implant) or cartilage flap that is implanted into a cartilage and bone defect. It is fixed to the subchondral bone using a second embodiment of the present invention directed perpendicularly to the articulating surface.
Figure 9:
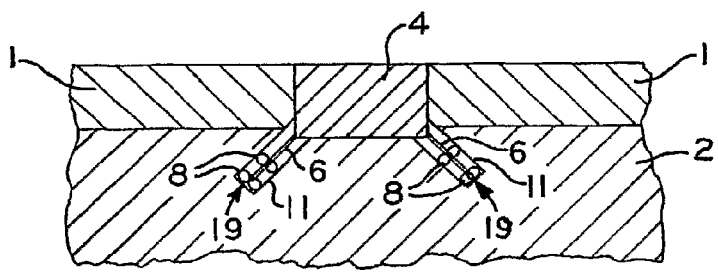
FIG. 9 is a cross sectional schematic of a cartilage repair device (or implant) or cartilage flap that is implanted into a cartilage and bone defect. It is fixed to the subchondral bone using a second embodiment of the present invention directed at an angle that is not perpendicular to the articulating surface.
Figure 10:
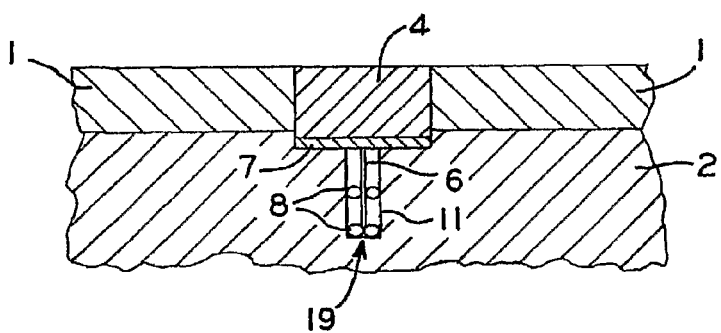
FIG. 10 is a cross sectional schematic of a cartilage repair device (or implant) or cartilage flap with a rigid or semi-rigid base that is attached to the implant. The assembly is implanted into a cartilage and bone defect. It is fixed to the subchondral bone using a second embodiment of the present invention directed at an angle that is not perpendicular to the articulating surface.
Figure 23:
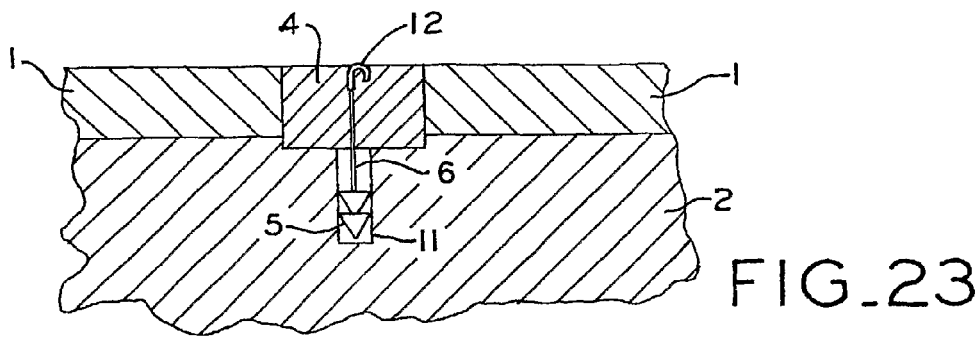
FIG. 23 is a cross sectional schematic of a cartilage repair device (or implant) or cartilage flap that is implanted into a cartilage and bone defect. It is fixed to the subchondral bone using the sixth embodiment of the present invention.
Figure 25:
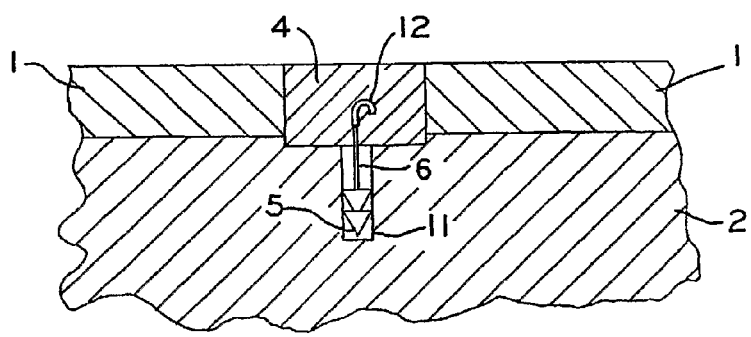
FIG. 25 is a cross sectional schematic of a cartilage repair device (or implant) or cartilage flap that is implanted into a cartilage and bone defect. It is fixed to the subchondral bone using the sixth embodiment of the present invention.
Figure 26:
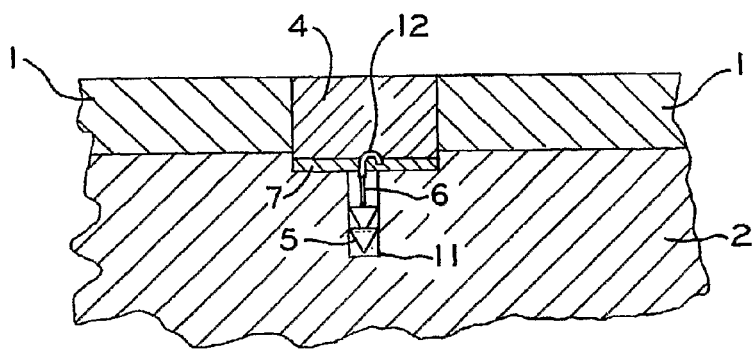
FIG. 26 is a cross sectional schematic of a cartilage repair device (or implant) or cartilage flap with a rigid or semi-rigid base that is attached to the implant. The assembly is implanted into a cartilage and bone defect. It is fixed to the subchondral bone using the sixth embodiment of the present invention.
Figure 31:
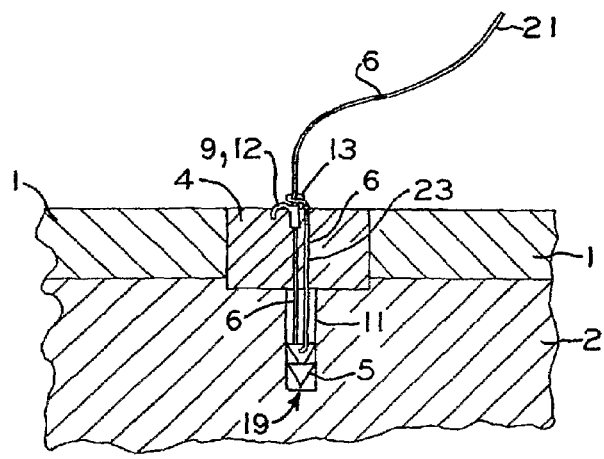
FIG. 31 is a cross sectional schematic of a cartilage repair device (or implant) or cartilage flap that is implanted into a cartilage and bone defect. It is fixed to the subchondral bone using the eighth embodiment of the present invention.
Figure 33:
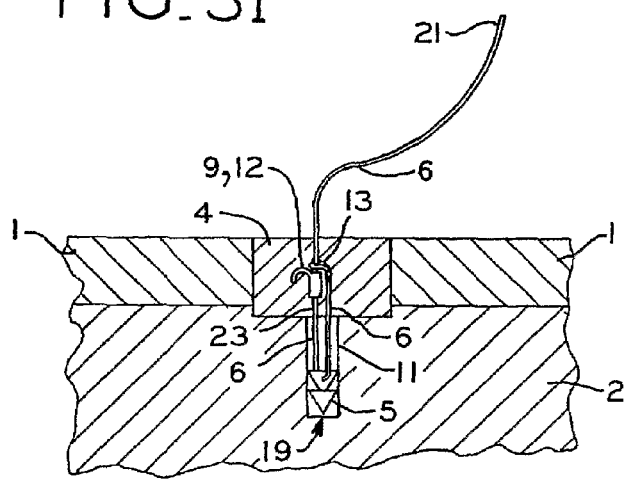
FIG. 33 is a cross sectional schematic of a cartilage repair device (or implant) or cartilage flap that is implanted into a cartilage and bone defect. It is fixed to the subchondral bone using the eighth embodiment of the present invention.
Figure 34:
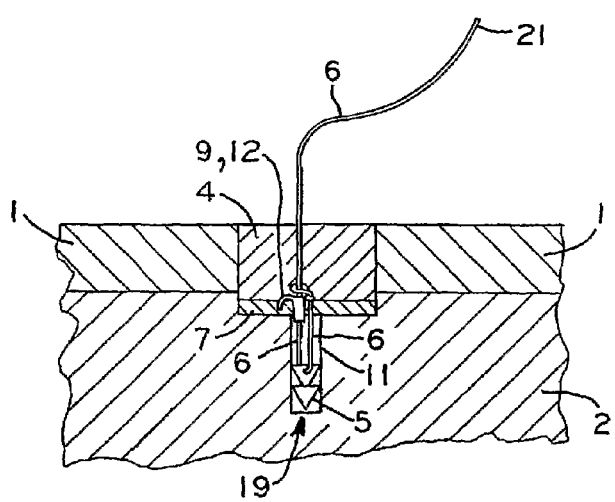
FIG. 34 is a cross sectional schematic of a cartilage repair device (or implant) or cartilage flap with a rigid or semi-rigid base that is attached to the implant. The assembly is implanted into a cartilage and bone defect. It is fixed to the subchondral bone using the eighth embodiment of the present invention.

A variety of articular cartilage fixation devices 19 utilizing the principles of the present invention are illustrated in the accompanying drawings. The illustrated surgical devices 19 are intended for implantation in a patient for repairing a tissue of the body in the patient. The illustrated embodiments would most commonly be used in repairing articular cartilage, such as that in the knee, hip, shoulder, or ankle; however, the invention is not so limited. Articular cartilage and subchondral bone are illustrated at 1 and 2, respectively, in the accompanying drawings (FIGS. 1-3,5-7, 9-11, 13-15, 17-19, 21-23, 25-27, 29-31, 33-36, 40-42). An example of a cartilage and bone defect is shown in FIGS. 1-3,5-7, 9-11, 13-15, 17-19, 21-23, 25-27, 29-31, and 33-36, 40-42. The invention is also expected to be useful in the treatment of cartilage only defects (i.e. defects without the involvement of bone) and in the treatment of damaged or diseased cartilage in other body parts as well.

As used herein "surgical device" refers to the fact that the surgical fixation devices 19 include at least one fixating element 5 and at least one flexible member 6 as an integral unit prior to the time that the surgical devices are implanted in the patient. Preferably, each fixation device 19 is attached to or is an integral member of the cartilage repair device (or implant) or cartilage flap 4. Therefore, for example, suture may be incorporated into the device prior to the time the device is implanted in the patient. However, it should be understood that although at least one of each element is included in the device, the surgeon may choose to use additional material during the surgery. For example, the surgeon may choose during surgery to use an additional fixation mechanism that was not an integral part of the original device if the surgeon thinks that additional stabilization is required or desired.

As used herein, bioresorbable, resorbable, bioabsorbable, and absorbable are intended to be interchangeable. All four terms are intended to mean materials that are naturally degradable in vivo over time. All are intended to include both natural and man-made materials and to include new materials, as they are developed, unless a specific material or a type of material are identified in the claims.

Figure 8:
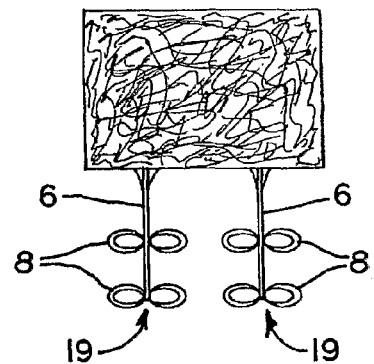
FIG. 8 is a cross sectional schematic of a cartilage repair device (or implant) or cartilage flap with a second embodiment of the present invention shown as an integral part of or is attached to the cartilage repair device (or implant) or cartilage flap.

Referring now to the illustrated embodiments of the present invention, one group of surgical devices 19 is illustrated in FIGS. 3-10. As illustrated in FIGS. 3-10, the surgical fixation devices 19 are an integral part or are attached to the cartilage repair device (or implant) or cartilage flap 4. As illustrated in FIGS. 3-10, each surgical fixation device includes an anchor 5 or an anchor knot 8 attached to a flexible member 6, and the flexible member 6 is attached to the cartilage repair device (or implant) or cartilage flap 4 directly or via a rigid or semi-rigid base 7 that is in turn attached to the cartilage repair device (or implant) or cartilage flap 4. The anchor 5 or anchor knot 8 is intended to anchor into subchondral bone 2 or into adjacent cartilage tissue 1. Since the surgical device 19 is an integral part of or is attached to the cartilage repair device (or implant) or cartilage flap 4 and since the anchor 5 or anchor knot 8 is anchored into the subchondral bone or into the adjacent cartilage, the surgical device 19 acts to fixate the cartilage repair device (or implant) or cartilage flap 4 to the chondral (cartilage) or osteochondral (cartilage and bone) defect area such that healing can occur.

Figure 24:
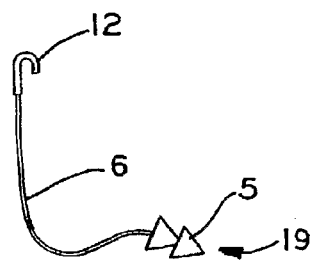
FIG. 24 is a perspective view of the sixth embodiment of the present invention.

A second group of surgical devices 19 is illustrated in FIGS. 11-26 & 38. As illustrated in FIGS. 11-26 & 38, the surgical devices 19 are not necessarily an integral member of the cartilage repair device (or implant) or cartilage flap 4. Each surgical fixation device 19 includes an anchor 5 or an anchor knot 8 attached to a flexible member 6, and the flexible member 6 retains the cartilage repair device (or implant) or cartilage flap 4 directly or via retaining a rigid or semi-rigid base 7 that is in turn attached to the cartilage repair device (or implant) or cartilage flap 4. Retaining of the cartilage repair device (or implant) or cartilage flap 4 or rigid or semi-rigid base 7 is achieved with a retaining component 9 on the proximal end of flexible member 6. The retaining component 9 prevents the surgical device 19 from totally passing through the cartilage repair device (or implant) or cartilage flap 4 and retains the cartilage repair device (or implant) or cartilage flap 4 directly or via retaining the rigid or semi-rigid base 7 that in turn is attached to the cartilage repair device (or implant) or cartilage flap 4. The retaining component 9 in this group is preferably a knot or knots of nonwoven, woven, and/or knitted pieces of biocompatible material (FIG. 38) that are attached to the flexible member. Another embodiment that is in this group includes the use of a wedging component 10 at the distal end of the flexible member 6 to lock the anchor knot 8 or anchor 5 into the hole 11 in the subchondral bone 2. The wedging component 10 could be in the shape of a bead, rectangle, cube, oval, triangle, trapezoidal and is manufactured from a biocompatible material. The wedging component 10 could also be nonwoven, woven, and/or knitted pieces of biocompatible material that may or may not be attached to the flexible member.

Figure 32:
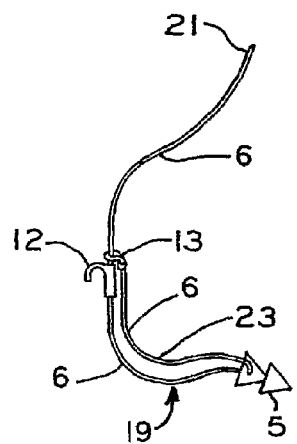
FIG. 32 is a perspective view of the eighth embodiment of the present invention.

A third group of surgical devices 19 is illustrated in FIGS. 27-34. As illustrated in FIGS. 27-34, the surgical devices 19 are not necessarily an integral member of the cartilage repair device (or implant) or cartilage flap 4. Each surgical fixation device 19 includes an anchor 5 through which a flexible member 6 is looped 23. The flexible member is attached back on to the free proximal end 21 of the flexible member 6 via a slip knot or sliding device 13 such that when a tensile force is applied to the free proximal end 21 of the flexible member 6 the slip knot or sliding device 13 travels distally down the flexible member 6 while the anchor 5 which is fixed to the subchondral bone 2 or native cartilage 1 acts as a pulley. In FIGS. 27-30, the slip knot or sliding device 13 is appropriately sized such that the slip knot or sliding device 13 does not slide completely through the cartilage repair device (or implant) or cartilage flap 4 but rather such that the slip knot or sliding device 13 lodges on top or within the cartilage repair device (or implant) or cartilage flap 4, thereby fixing the cartilage repair device (or implant) or cartilage flap 4 into the chondral or osteochondral defect 3. In FIGS. 31-34, a retaining device 12 is distally located from the slip knot or sliding device 13 such that when the slip knot or sliding device 13 slides distally down the flexible member 6 the slip knot or sliding device 13 pushes the retaining device 12 down the flexible member 6 also. As the retaining device 12 is pushed down the flexible member 6, it engages onto or into the cartilage repair device (or implant) or cartilage flap 4 and fixates it in the chondral or osteochondral defect 3. The slip knot or sliding device 13 then locks in place when seated on or with the cartilage repair device (or implant) or cartilage flap 4.

A fourth group of surgical devices 19 is illustrated in FIGS. 35-36. As illustrated in FIGS. 35-36, the surgical devices 19 are not necessarily an integral member of the cartilage repair device (or implant) or cartilage flap 4. Each surgical fixation device 19 includes an anchor 5 through which a flexible member 6 is looped 23. The distal attachment end 14 of the flexible member 6 is attached to the cartilage repair device (or implant) or cartilage flap 4 or to a rigid or semi-rigid base 7 which is in turn attached to the cartilage repair device (or implant) or cartilage flap 4; whereas, the proximal end 21 of the flexible member 6 is free and passes through the cartilage repair device (or implant) or cartilage flap 4. After fixating the anchor 5 into the subchondral bone 2 or native articular cartilage 1, the anchor 5 resists pulling forces from the proximal end 21 of the flexible member 6 and acts as a pulley; therefore, when a tensile force is applied to the proximal end 21 of the flexible member 6, the resultant action is that the cartilage repair device (or implant) or cartilage flap 4 is pulled by the distal attachment point 14 of the flexible member 6 and fixated into the chondral or osteochondral defect area 3. The flexible member 6 is then locked in place via a wedging component 10 applied against the flexible member 6 within the subchondral bone hole 11 or native cartilage hole and proximal to the anchor 5. Alternatively, the wedging component 10 could also be applied against the flexible member 6 within the rigid or semi-rigid base 7 that could be attached to the cartilage repair device (or implant) or cartilage flap 4 such that the flexible member 6 is fixated to or within the rigid or semi-rigid base 7 and in turn fixates the cartilage repair device (or implant) or cartilage flap 4 because of its attachment to the rigid or semi-rigid base 7. The wedging component 10 could be in the shape of a bead, rectangle, cube, oval, triangle, trapezoidal and is manufactured from a biocompatible material. The wedging component 10 could also be a nonwoven piece of biocompatible material that may or may not be attached to the flexible member or a woven piece of biocompatible material that may or may not be attached to the flexible member or a knitted piece of biocompatible material that may or may not be attached to the flexible member or any combination of the above.

A fifth group of surgical devices 19 is illustrated in FIGS. 44-45. As illustrated in FIGS. 44-45, the surgical devices 19 are attached to the cartilage repair device (or implant) or cartilage flap 4 at attachment point 14. Each surgical fixation device 19 includes an anchor 5 through which a flexible member 6 is looped twice 24. The distal attachment end 14 of the flexible member 6 is attached to the cartilage repair device (or implant) or cartilage flap 4 or to a rigid or semi-rigid base 7 which is in turn attached to the cartilage repair device (or implant) or cartilage flap 4; whereas, the proximal end 21 of the flexible member 6 is threaded through the anchor 5 and looped proximally and then looped distally and threaded through the anchor 5 again such that the free end of the flexible member 6 traverses proximally and attaches proximally to the first loop via a slip knot or sliding device 13. After fixating the anchor 5 into the subchondral bone 2 or native articular cartilage 1, the anchor 5 resists pulling forces from the proximal end loop 25 of the flexible member 6 and acts as a pulley; therefore, when a tensile force is applied to the proximal end of the loop 25 of the flexible member 6, the resultant action is that the cartilage repair device (or implant) or cartilage flap 4 is pulled by the distal attachment point 14 of the flexible member 6 and fixated into the chondral or osteochondral defect area 3 as the flexible member 6 slides through the anchor 5. The flexible member 6 is then locked in place when the slip knot or sliding device 13 is seated against or within the cartilage repair device (or implant) or cartilage flap 4.

A variety of materials may be used for the anchors 5, knots 8, wedging components 10, retaining devices 9, and retaining devices 12. For example, they could be manufactured from biocompatible polymers, biocompatible collagenous matrices, and/or any combination thereof. Other materials such as bioactive agents, biologically derived agents, inorganic materials that are biocompatible, cells, and biological lubricants can also be included as part of these components. Note that biocompatible polymers is intended to include both synthetic polymers and biologically derived polymers (i.e. collagen). Some examples of biocompatible polymers include: polyesters; poly-L-lactic acid (PLLA); polyglycolic acid (PGA); polydioxinone (PDS or PDO); polycaprilactone (PCL); polyvinyl alcohol (PVA); polyethylene oxide (PEO); polymers disclosed in U.S. Pat. Nos. 6,333,029 and 6,355,699; polymers derived from tyrosine; polymers derived from chitosan; polymers derived from collagenous tissues; any other biocompatible polymer that is or is not bioabsorbable, or copolymer, or mixture of polymers or co-polymers that are used in the construction of implants. In addition, as new biocompatible materials that may be or may not be bioabsorbable are developed, it is expected that at least some of them will be useful materials from which at least some of these components could be made. Note that the above materials are identified by way of example only, and the present invention is not limited to any particular material unless expressly called for in the claims.

Where the present invention includes at least one flexible member 6 that includes or consists of suture, any suitable suture material may be used, such as is commercially available suture. Acceptable suture may be obtained from Ethicon, Inc. of Sommerset, N.J.; examples include Vicryl® absorbable suture, Panacryl® absorbable suture, Ethibond® polyester, Prolene® polypropylene suture, and PDS polydioxanone suture.

When referring to attachment points where one component is attached to another (i.e. the anchor 5 attached to the flexible component 6), the attachment could be accomplished in a variety of methods. For example, the flexible member 6 could be tied to the anchor 5 or the flexible anchor 6 could be molded as an integral part of anchor 5, or the flexible member 6 could be glued to the anchor 5, or flexible member 6 could be mechanically locked to the anchor 5. Similarly, the same modes or others could be utilized when attaching the flexible member to the rigid or semi-rigid base 7 or when attaching any component in the present invention to another or to the cartilage repair device (or implant) or cartilage flap 4. Note that the present invention is not limited to any particular mode of attachment.

The first group of illustrated surgical fixation devices 19, as illustrated in FIGS. 3-10, is useful for surgical implantation of an articular cartilage repair device (or implant) 4. The objective with each of these devices is similar: to position the anchor 5 or anchor knot 8 into the subchondral bone 2 and/or adjacent native cartilage 1 such that the cartilage repair device (or implant) 4 is fixated into the chondral or osteochondral defect area 3. For these embodiments, the hole in the subchondral bone 2 or cartilage 1 could be made with a punch, needle, drill, awl, microfracture instrument, Steinman pin, k-wire, laser, Rf wand, etc. . . . prior to implantation of the surgical fixation device 19 or the hole in the subchondral bone 2 or cartilage 1 could be make by the anchor 5 supported by an insertion instrument 22 as shown by example in FIG. 37. For these embodiments, a surgical kit would generally be provided with one or more fixation devices 19 attached to or as an integral part of the cartilage repair device (or implant) 4. The cartilage defect 3, 20 is evaluated and is prepared in a standard manner either to or through a portion of the subchondral bone. From the initial evaluation, the surgeon determines the size to which he would need to either trim the defect or trim the cartilage repair device (or implant) 4 and then would trim the appropriate item to the appropriate size. Using the embodiments illustrated in FIGS. 3-10, at least one anchor, such as anchor 5, positioned and fixated into the subchondral bone 1 or cartilage 2 either creating its own hole 11 or into a previously prepared hole 11 with the flexible member or suture 6 tethering the cartilage repair device (or implant) or cartilage flap 4 into the chondral or osteochondral defect 3. The anchor 5 or anchor knot 8 is pushed far enough into the subchondral bone 2 or cartilage 1 to approximate the distal surface of the cartilage repair device (or implant) or cartilage flap 4 and the proximal surface of the chondral or osteochondral defect 3. For these embodiments, the insertion instrument could simply be a cylindrical rod that pushes against the proximal surface of the anchor 5 or anchor knot 8 or it could be a more complex instrument that includes tubular needles and cables or similar structures used for actuation via a trigger or similar device during implantation of the device. For instance, the surgeon could push the anchor 5 through the subchondral bone, thus, creating the hole and positioning the anchor, until the tension in the flexible member or suture 6 is adequate to fixate the cartilage repair device (or implant) 4.

The second group of illustrated surgical fixation devices 19, as illustrated in FIGS. 11-26, is useful for surgical implantation of articular cartilage repair device (or implant) or cartilage flap 4. The objective with each of these devices is similar: to position the anchor 5 or anchor knot 8 into the subchondral bone 2 and/or adjacent native cartilage 1 such that the proximal retaining component 9, 12 retains the cartilage repair device (or implant) or cartilage flap 4 and, thus, fixates the cartilage repair device (or implant) or cartilage flap 4 is fixated into the chondral or osteochondral defect area 3. For these embodiments, the hole in the subchondral bone 2 or cartilage 1 could be made with a punch, needle, drill, awl, microfracture instrument, Steinman pin, k-wire, laser, Rf wand, etc. . . . prior to implantation of the surgical fixation device 19 or the hole in the subchondral bone 2 or cartilage 1 could be made by the anchor 5 supported by an insertion instrument 22 as shown by example in FIG. 37. For these embodiments, a surgical kit would generally be provided with one or more fixation devices 19. The cartilage defect 3, 20 is evaluated and is prepared in a standard manner either to or through a portion of the subchondral bone. From the initial evaluation, the surgeon determines the size to which he would need to either trim the defect or trim the cartilage repair device (or implant) or cartilage flap 4 and then would trim the appropriate item to the appropriate size. Using the embodiments illustrated in FIGS. 11-26 at least one anchor, such as anchor 5, is positioned and fixated into the subchondral bone 1 or cartilage 2 either creating its own hole 11 or into a previously prepared hole 11 with the flexible member or suture 6 passing either partially or completely through the cartilage repair device (or implant) or cartilage flap 4 such that the retaining device 9 on the proximal end of the flexible member or suture 6 directly retains the cartilage repair device (or implant) or cartilage flap 4 in the chondral or osteochondral defect 3 or indirectly retains the cartilage repair device (or implant) or cartilage flap by retaining a rigid or semi-rigid base that can be attached to the cartilage repair device (or implant) or cartilage flap 4. The anchor 5 or anchor knot 8 is pushed far enough into the subchondral bone 2 or cartilage 1 to approximate the distal surface of the cartilage repair device (or implant) or cartilage flap 4 and the proximal surface of the chondral or osteochondral defect 3. For these embodiments, the insertion instrument could simply be a cylindrical rod that pushes against the proximal surface of the anchor 5 or anchor knot 8 or it could be a more complex instrument that includes tubular needles and cables or similar structures used for actuation via a trigger or similar device during implantation of the device. For instance, the surgeon could push the anchor 5 through the subchondral bone, thus, creating the hole and positioning the anchor, until the tension in the flexible member or suture 6 is adequate to fixate the cartilage repair device (or implant) or cartilage flap 4. Also, the insertion instrument could be a device that is similar to the device 22 illustrated in FIG. 37. Insertion instrument 22 has a leading shaft 17 of a fixed length with a shoulder 16 positioned distally to the leading edge. The shoulder 16 is a result of having a stepped shaft 15 that is larger than the leading shaft 17. The purpose of the shoulder 16 is to act as a stop to control the depth to which the insertion instrument 22 inserts the surgical fixation device 19. The leading shaft 17 diameter is sized such that it will pass through a hole within the cartilage repair device (or implant) or cartilage flap 4 that is no larger than a hole that anchor 5 or anchor knot 8 will pass through. The purpose of the slot 18 is to contain the flexible member or suture 6 and the retaining device 9 during the delivery of the surgical fixation device 19. The fixed length of the leading shaft 17 could be adjustable such that different tissues and tissue properties could be accommodated.

The third group of illustrated surgical fixation devices 19, as illustrated in FIGS. 27-34, is useful for surgical implantation of articular cartilage repair device (or implant) or cartilage flap 4. The objective with each of these devices is similar: to position the anchor pulley 5 into the subchondral bone 2 and/or adjacent native cartilage 1 such that a tensile force can be applied to the free proximal end 21 of the looped flexible member or suture 6 such that the anchor pulley 5 will resist the force and not pull out. The flexible member is attached back on to the free proximal end 21 of the flexible member 6 via a slip knot 13 such that when the aforementioned tensile force is applied to the free proximal end 21 of the flexible member 6 the slip knot 13 travels distally down the flexible member 6 while the anchor 5 which is fixed to the subchondral bone 2 or native cartilage 1 acts as a pulley and remains fixated in the tissue. Either the slip knot 13 is appropriately sized such that the slip knot 13 does not slide completely through the cartilage repair device (or implant) or cartilage flap 4 but rather such that the slip knot 13 lodges on top or within the cartilage repair device (or implant) or cartilage flap 4, thereby fixing the cartilage repair device (or implant) or cartilage flap 4 into the chondral or osteochondral defect 3 or a retaining device 9 or retaining device 12 is distally located from the slip knot 13 such that when the slip knot 13 slides distally down the flexible member 6 the slip knot 13 pushes the retaining device 9 or retaining device 12 down the flexible member 6 also. As the retaining device 12 is pushed down the flexible member 6, it engages onto or into the cartilage repair device (or implant) or cartilage flap 4 and fixates it in the chondral or osteochondral defect 3. For these embodiments, the hole in the subchondral bone 2 or cartilage 1 could be made with a punch, needle, drill, awl, microfracture instrument, Steinman pin, k-wire, laser, Rf wand, etc. . . . prior to implantation of the surgical fixation device 19 or the hole in the subchondral bone 2 or cartilage 1 could be made by the anchor pulley 5 supported by an insertion instrument 22 as shown by example in FIG. 37. Once the anchor pulley 5 is positioned and fixated, the free proximal end 21 of the flexible member or suture 6 is pulled by the surgeon while pushing or not pushing the knot with a knot pusher until the fixation of the cartilage repair device (or implant) or cartilage flap 4 is adequate. For these embodiments, a surgical kit would generally be provided with one or more fixation devices 19. The cartilage defect 3, 20 is evaluated and is prepared in a standard manner either to or through a portion of the subchondral bone. From the initial evaluation, the surgeon determines the size to which he would need to either trim the defect or trim the cartilage repair device (or implant) or cartilage flap 4 and then would trim the appropriate item to the appropriate size. Using the embodiments illustrated in FIGS. 27-34 at least one anchor, such as anchor 5, is positioned and fixated into the subchondral bone 1 or cartilage 2 either creating its own hole 11 or into a previously prepared hole 11 with the flexible member or suture 6 passing through the cartilage repair device (or implant) or cartilage flap 4 such that the slip knot 13 and possibly the retaining device 9 or retaining device 12 on the proximal end of the flexible member or suture 6 directly retains the cartilage repair device (or implant) or cartilage flap 4 in the chondral or osteochondral defect 3 or retains the cartilage repair device (or implant) or cartilage flap by retaining a rigid or semi-rigid base that can be attached to the cartilage repair device (or implant) or cartilage flap 4. For these embodiments, the insertion instrument could simply be a cylindrical rod that pushes against the proximal surface of the anchor 5 or anchor knot 8 or it could be a more complex instrument that includes tubular needles and cables or similar structures used for actuation via a trigger or similar device during implantation of the device. For example a tubular needle and delivery instrument that is similar to that used with RAPIDLOC™ Meniscal Repair System that is owned by DePuy Mitek, a Johnson & Johnson Company, of Norwood, Mass. could be used for the delivery of the present invention. For instance, the surgeon could push the tubular needle into the subchondral bone, thus, creating the hole, and prior to retracting the needle, the surgeon would then deploy the anchor by pulling a trigger mechanism. The tubular needle and delivery instrument would then be removed from the surgical site. Then the surgeon would pull on the free proximal end 21 of the flexible member or suture 6 while pushing on the slip knot 13 with a knot pushing device similar to that used with RAPIDLOC™ Meniscal Repair System until the tension in the flexible member or suture 6 is adequate to fixate the cartilage repair device (or implant) or cartilage flap 4.

The fourth group of illustrated surgical fixation devices 19, as illustrated in FIGS. 35-36, is useful for surgical implantation of articular cartilage repair device (or implant) or cartilage flap 4. The objective with each of these devices is similar: to position the anchor pulley 5 into the subchondral bone 2 and/or adjacent native cartilage 1 such that a tensile force can be applied to the free proximal end 21 of the looped flexible member or suture 6 such that the anchor pulley 5 will resist the force and not pull out. The distal end 14 of the flexible member 6 is attached to the cartilage repair device (or implant) or cartilage flap 4 or to a rigid or semi-rigid base 7 that is attached to the cartilage repair device (or implant) or cartilage flap 4. When the aforementioned tensile force is applied to the free proximal end 21 of the flexible member 6 the anchor 5 acts as a pulley such that the flexible member 6 pulls through the anchor 5 and approximates the cartilage repair device (or implant) or cartilage flap 4 to the chondral or osteochondral defect 3, 20. Final fixation is accomplished by applying a wedging device 10 to lock the flexible member 6 within the subchondral bone hole 11 or native cartilage hole and proximal to the anchor 5. Alternatively, the wedging component 10 could also be applied against the flexible member 6 within the rigid or semi-rigid base 7 that is attached to the cartilage repair device (or implant) or cartilage flap 4 such that the flexible member 6 is fixated to or within the rigid or semi-rigid base 7 and in turn fix the cartilage repair device (or implant) or cartilage flap 4 because of its attachment to the rigid or semi-rigid base 7. For this embodiment, the hole in the subchondral bone 2 or cartilage 1 could be made with a punch, needle, drill, awl, microfracture instrument, Steinman pin, k-wire, laser, Rf wand, etc. . . . prior to implantation of the surgical fixation device 19 or the hole in the subchondral bone 2 or cartilage 1 could be made by the anchor pulley 5 supported by an insertion instrument 22 as shown by example in FIG. 37. Once the anchor pulley 5 is positioned and fixated, the free proximal end 21 of the flexible member or suture 6 is pulled by the surgeon while pushing or not pushing the knot with a knot pusher until the fixation of the cartilage repair device (or implant) or cartilage flap 4 is adequate. For this embodiment, a surgical kit would generally be provided with one or more fixation devices 19. The cartilage defect 3, 20 is evaluated and is prepared in a standard manner either to or through a portion of the subchondral bone. From the initial evaluation, the surgeon determines the size to which he would need to either trim the defect or trim the cartilage repair device (or implant) or cartilage flap 4 and then would trim the appropriate item to the appropriate size. Using the embodiments illustrated in FIGS. 27-34 at least one anchor, such as anchor 5, is positioned and fixated into the subchondral bone 1 or cartilage 2 either creating its own hole 11 or into a previously prepared hole 11 with the free proximal end 21 of the flexible member or suture 6 passing completely through the cartilage repair device (or implant) or cartilage flap 4. For this embodiment, the insertion instrument could simply be a cylindrical rod that pushes against the proximal surface of the anchor 5 or anchor knot 8 or it could be a more complex instrument that includes tubular needles and cables or similar structures used for actuation via a trigger or similar device during implantation of the device. For example a tubular needle and delivery instrument that is similar to that used with RAPIDLOC™ Meniscal Repair System that is owned by DePuy Mitek, a Johnson & Johnson Company, of Norwood, Mass. could be used for the delivery of the present invention. For instance, the surgeon could push the tubular needle into the subchondral bone, thus, creating the hole, and prior to retracting the needle, the surgeon would then deploy the anchor by pulling a trigger mechanism. The tubular needle and delivery instrument would then be removed from the surgical site. Then the surgeon would pull on the free proximal end 21 of the flexible member or suture 6 to position the cartilage repair device (or implant) or cartilage flap 4 at which time the surgeon would then apply the wedging device 10 into the subchondral bone or cartilage hole 11 such that the tension in the flexible member or suture 6 is adequate to fixate the cartilage repair device (or implant) or cartilage flap 4 in the chondral or osteochondral defect 3,20.

The fifth group of illustrated surgical fixation devices 19, as illustrated in FIGS. 44-45, is useful for surgical implantation of articular cartilage repair device (or implant) or cartilage flap 4. The objective with each of these devices is similar: to position the anchor pulley 5 into the subchondral bone 2 and/or adjacent native cartilage 1 such that a tensile force can be applied to the proximal loop end 25 of the double-looped flexible member or suture 24 such that the anchor pulley 5 will resist the force. The distal end 14 of the flexible member 6 is attached to the cartilage repair device (or implant) or cartilage flap 4 or to a rigid or semi-rigid base 7 that is attached to the cartilage repair device (or implant) or cartilage flap 4. When the aforementioned tensile force is applied to the proximal loop end 25 of the flexible member 6, the anchor 5 acts as a pulley such that the flexible member 6 pulls through the anchor 5 and approximates the cartilage repair device (or implant) or cartilage flap 4 to the chondral or osteochondral defect 3, 20, while the slip knot or sliding device 13 traverses down the proximal loop end 25. Final fixation is accomplished when the slip knot or sliding device reaches the cartilage repair device (or implant) or cartilage flap 4 and tension is applied to the assembly such the slip knot or sliding device 13 locks the flexible member or suture 6 in place, thereby locking the cartilage repair device (or implant) or cartilage flap 4 in the chondral or osteochondral defect. For this embodiment, the hole in the subchondral bone 2 or cartilage 1 could be made with a punch, needle, drill, awl, microfracture instrument, Steinman pin, k-wire, laser, Rf wand, etc. . . . prior to implantation of the surgical fixation device 19 or the hole in the subchondral bone 2 or cartilage 1 could be made by the anchor pulley 5 supported by an insertion instrument 22 as shown by example in FIG. 37. Once the anchor pulley 5 is positioned and fixated, the proximal looped end 25 of the flexible member or suture 6 is pulled by the surgeon while pushing or not pushing the knot with a knot pusher until the fixation of the cartilage repair device (or implant) or cartilage flap 4 is adequate. For this embodiment, a surgical kit would generally be provided with one or more fixation devices 19 that would be pre-attached to the cartilage repair device (or implant) or cartilage flap 4 or would be attached at the time of surgery. The cartilage defect 3, 20 is evaluated and is prepared in a standard manner either to or through a portion of the subchondral bone. From the initial evaluation, the surgeon determines the size to which he would need to either trim the defect or trim the cartilage repair device (or implant) or cartilage flap 4 and then would trim the appropriate item to the appropriate size. Using the embodiments illustrated in FIGS. 43-45 at least one anchor, such as anchor 5, is positioned and fixated into the subchondral bone 1 or cartilage 2 either creating its own hole 11 or into a previously prepared hole 11 with the free proximal end 21 of the flexible member or suture 6 passing completely through the cartilage repair device (or implant) or cartilage flap 4. For this embodiment, the insertion instrument could simply be a cylindrical rod that pushes against the proximal surface of the anchor 5 or it could be a more complex instrument that includes tubular needles and cables or similar structures used for actuation via a trigger or similar device during implantation of the device. For example a tubular needle and delivery instrument that is similar to that used with RAPIDLOC™ Meniscal Repair System that is owned by DePuy Mitek, a Johnson & Johnson Company, of Norwood, Mass. could be used for the delivery of the present invention. For instance, the surgeon could push the tubular needle into the subchondral bone, thus, creating the hole, and prior to retracting the needle, the surgeon would then deploy the anchor by pulling a trigger mechanism. The tubular needle and delivery instrument would then be removed from the surgical site. Then the surgeon would pull on the proximal looped end 25 of the flexible member or suture 6 to position the cartilage repair device (or implant) or cartilage flap 4 at which time the surgeon would then apply tension on the proximal looped end 25 while pushing on the slip knot or sliding device 13 with a knot pusher until the slip knot or sliding device 13 is locked in place, thus locking the cartilage repair device (or implant) or cartilage flap in the defect 3,20.

I claim:

1. A surgical device for repairing cartilage tissue at a defect site in a patient, said surgical device comprising:
a first biocompatible anchor shaped to sit within tissue at the defect site and retain a section of cartilage replacement material in the defect site;
a biocompatible flexible member traversing through said section of cartilage replacement material multiple times, a distal end of said flexible member mechanically locked to said section of cartilage replacement material at an attachment point and a proximal end of said flexible member threaded through said first biocompatible anchor at least twice to form at least two pulley mechanisms; and
a sliding device about said flexible member, the proximal end of the flexible member at least in part forming the sliding device, and the portion of the flexible member extending between the distal end and the sliding device traverses through the section of cartilage replacement material at least three times, wherein, when in use, the at least two pulley mechanisms are actuated to translate the sliding device distally along said flexible member to a position proximate said section of cartilage replacement material to locate and retain said section of cartilage replacement material in the defect site.

2. The device of claim 1, wherein said sliding device comprises a slipknot fashioned about said flexible member which, when tensioned about said flexible member, retains said section of cartilage replacement material in the defect site.

3. The device of claim 1, wherein said section of cartilage replacement material is formed at least in part of a material selected from the group consisting of non-woven materials and foam materials.

4. The device of claim 1, wherein said section of cartilage replacement material is formed at least in part of a synthetic polymer selected from the group consisting of polyesters and co-polymers of polyesters.

5. The device of claim 1, wherein said section of cartilage replacement material is a scaffold derived from at least one biological material selected from the group consisting of proteins, saccharides, and collagenous tissue.

6. The device of claim 1, wherein said flexible member is a braided suture.

7. The device of claim 1, wherein said sliding device comprises a stopping member, said stopping member being engageable with said section of cartilage replacement material.

8. The device of claim 1, wherein said stopping device is engageable with a proximal surface of the section of cartilage replacement material.

9. The device of claim 4, wherein the polyesters and co-polymers of polyesters are at least one of poly-L-lactic acid (PLLA), poly-D-lactic acid (D-PLA), polyglycolic acid (PGA), polydioxinone (PDO), polycaprolactone (PCL), polyvinyl alcohol (PVA), polyethylene oxide (PEO), and poly (etheylene terephthalate).

10. The device of claim 5, wherein the proteins are at least one of tyrosine and polysaccharides, and the saccharides are at least one of chitosan and hyaluronic acid.

11. The device of claim 1, wherein the at least two pulley mechanisms comprise a proximal looped end and two distal loops with the proximal looped end positioned through the sliding device, and wherein, upon tensioning of the proximal looped end, the two distal loops corresponding slide thorough the anchor to facilitate decreasing the distance between said attachment point and said anchor thereby positioning said section of cartilage replacement material in the defect site.

12. The device of claim 1, wherein the section of cartilage replacement material comprises a scaffold, the scaffold being fabricated from a biocompatible material for facilitating at least one of chondral and osteochondral integration.

13. The device of claim 1, wherein the device further comprises the section of cartilage replacement material.

14. The device of claim 1, wherein the sliding device comprises a lockable sliding device.

15. The device of claim 1, wherein mechanically locked comprises at least one of tied to the section of cartilage replacement material, integrally molded with the section of cartilage replacement material, glued to the section of cartilage replacement material, and attached to a base attached to the section of cartilage replacement material.

16. The device of claim 1, wherein the biocompatible anchor is positioned proximate a first side of the section of cartilage replacement material, and the sliding device is positioned proximate a second side of the section of cartilage replacement material that substantially opposes the first side of the section.

17. The device of claim 1, wherein each of the at least two pulley mechanisms include two member portions of the flexible member extending from the anchor, and wherein at least one member portion of one pulley mechanism traverses the cartilage replacement material, and both member portions of the other pulley mechanism traverse the cartilage replacement material.

18. The device of claim 1, wherein the total length of the flexible member extending between the sliding device and the attachment point remains the same both before and after the section of cartilage replacement material is located and retained in the defect site.

19. The device of claim 1, wherein the threading of the flexible member through the anchor at least twice to form at least two pulley mechanisms also forms at least, one loop between two adjacent pulley mechanisms, and wherein the sliding device is formed about the at least one loop.

20. The device of claim 1, wherein the threading of the flexible member through the anchor at least twice to form at least two pulley mechanisms also forms at least one loop between two adjacent pulley mechanisms, and wherein the at least one loop is enlarged to locate and retain the section of cartilage replacement material in the defect site.

21. The device of claim 1, wherein the sliding device is located at the proximal end of the flexible member both before and after the section of cartilage replacement material is located and retained in the defect site.

22. The device of claim 1, wherein the attachment point is positioned proximate a first side of the section of cartilage replacement material, and the sliding device is positioned proximate a second side of the section of cartilage replacement material that substantially opposes the first side of the section.

* * * * *